United States Patent [19]
Claybaugh et al.

[11] Patent Number: 5,699,436
[45] Date of Patent: Dec. 16, 1997

[54] HANDS FREE NOISE CANCELING HEADSET

[75] Inventors: David Claybaugh, Germantown, Md.; Jeffrey N. Denenberg, Trumbull, Conn.

[73] Assignee: Noise Cancellation Technologies, Inc., Linthicum, Md.

[21] Appl. No.: 325,397

[22] PCT Filed: Apr. 30, 1992

[86] PCT No.: PCT/US92/03441

§ 371 Date: Oct. 27, 1994

§ 102(e) Date: Oct. 27, 1994

[87] PCT Pub. No.: WO93/21876

PCT Pub. Date: Nov. 11, 1993

[51] Int. Cl.$^6$ .................................................. G10K 11/16
[52] U.S. Cl. .................................................. 381/71; 381/94
[58] Field of Search ................................. 381/71, 72, 74, 381/94, 103, 155; 181/206; 379/406, 407, 410, 412, 387, 388, 390, 395

[56] References Cited

U.S. PATENT DOCUMENTS

| | | |
|---|---|---|
| 2,972,018 | 2/1961 | Hawley et al. . |
| 4,258,235 | 3/1981 | Watson ................... 381/155 |
| 4,654,871 | 3/1987 | Chaplin ................... 381/72 |
| 4,677,677 | 6/1987 | Eriksson . |
| 4,736,432 | 4/1988 | Cantrell . |
| 4,953,217 | 8/1990 | Twiney et al. . |
| 4,977,600 | 12/1990 | Ziegler . |
| 5,001,763 | 3/1991 | Moseley . |
| 5,033,082 | 7/1991 | Eriksson et al. . |
| 5,046,103 | 9/1991 | Warnaka ................... 381/71 |
| 5,091,954 | 2/1992 | Sasaki et al. . |
| 5,105,377 | 4/1992 | Ziegler ................... 381/71 |
| 5,182,774 | 1/1993 | Bourk ................... 381/74 |
| 5,402,497 | 3/1995 | Nishimoto ................... 381/74 |
| 5,481,615 | 1/1996 | Eatwell ................... 381/71 |

*Primary Examiner*—Curtis Kuntz
*Assistant Examiner*—Min Oh Harvey

[57] ABSTRACT

In the area of active noise cancellation headsets, the noisy environment often encountered in the link with communication systems causes lack of intelligibility on the outward communications path. Consequently another in-wire cancellation channel to enhance the intelligibility is required. This additional processing channel adds to the cost of the headset. The invention uses residual microphones (12) to reproduce the sound that remains in the ear after cancellation so that the controller (13) can make further adjustments through filter (15) and LMS adapter (14) to the anti-noise signal.

7 Claims, 2 Drawing Sheets

HANDS FREE NOISE CANCELING HEADSET

In the area of active noise cancellation headsets, the noisy environment often encountered in the link with communication systems causes lack of intelligibility on the outward communications path. Consequently another in-wire cancellation channel to enhance the intelligibility is required. This additional processing channel adds to the cost of the headset. "In-wire" cancellation refers to any of the active control approaches that performs the cancellation of noise in a manner such as that described in U.S. patent application No. 07/421,759, which is hereby incorporated by reference therein.

The instant invention contemplates the use of the headset residual microphones to pick up the user's speech for communications. It utilizes two separate noise canceling systems both having a residual microphone located at the ear to sense any noise remaining. They also use a controller which synthesizes the anti-noise signal and a headset driver to deliver the anti-noise signal to the ear vicinity. The algorithm used is the one described in U.S. Pat. No. 5,105,377, which is a digital virtual earth algorithm which develops a reference signal by subtracting an equalized anti-noise signal of its own from the residual signal.

Accordingly, an object of this invention is to provide an active noise cancellation headset in which the residual microphone is used to pick-up the user's speech for communication.

A further object of this invention is to use a small electret microphone in an active noise cancellation headset to improve voice intelligibility.

Another object of this invention is to provide a hands-free active noise canceling headset where the outward communication path is handled by microphones in the earpieces.

These and other objects will become apparent when reference is had to the accompanying description and drawings in which.

Figure 1:
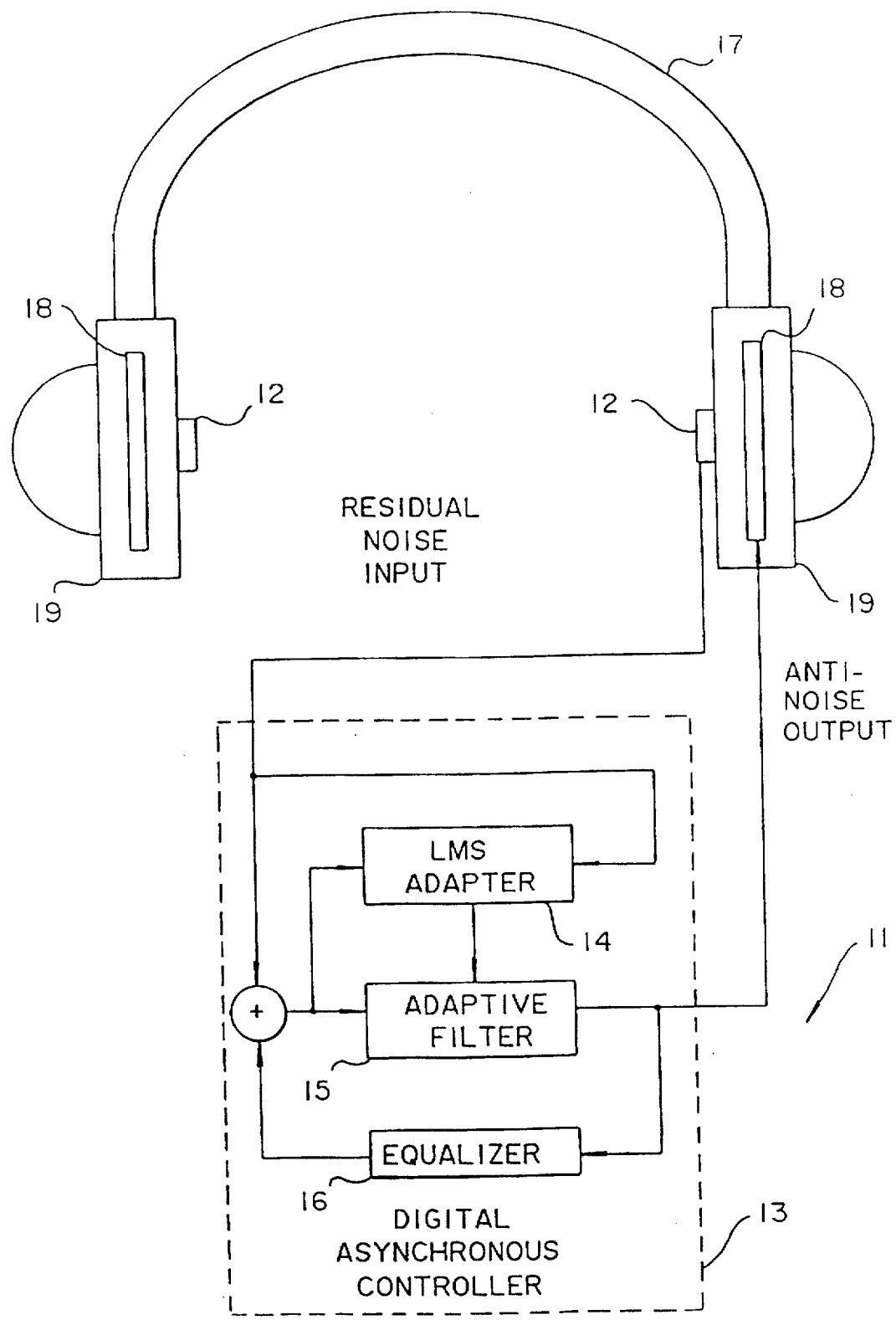
FIG. 1 is a diagrammatic view of the headset of this invention and the circuitry therefore.

An active noise canceling headset system is shown in FIG. 1 as 10. It consists of two independent noise canceling/systems, such as 11 (only one is shown in the figure), each of which has a residual microphone 12 located at the ear to sense any remaining noise, a system controller 13 to synthesize the anti-noise signal and a headset driver to deliver the anti-noise to the vicinity of the ear. The system components: an LMS (Least Means Square) adapter 14, an adaptive filter 15 and an equalizer 16.

The headset 17 has an open back. This is the most desirable configuration since it is the lightest in weight and, given the selective nature of our noise canceling algorithms, allows the wearer to hear warning signals and external communications thereby increasing user safety.

It has anti-noise speakers 18 to generate sound to cancel unwanted environment noise.

The algorithm used is the digital virtual earth algorithm which develops a reference signal by subtracting an equalized version of its own anti-noise signal from the residual signal. It has been shown to be highly effective in headsets for simple noise environments (a small number of harmonics) even when the noise signal is rapidly varying (as in a siren noise canceling headset). The Least Means Square (LMS) adaption shown is a Filtered-X version which has inherent compensation for the effects of the feedback delays around the loop.

The headset driver (or speaker) is capable of producing the anti-noise at the same level as the noise to be cancelled. It has little or no distortion and has a minimum of input-to-output delay as any delay in the feedback loop slows down the system adaptation rate.

The residual microphone 12 is typically a small electret (capacitive) microphone that is mounted on the driver frame 19 near the ear. It faithfully reproduces the sound that remains at the ear after cancellation so that the controller can make further adjustments to the anti-noise signal.

An example of an application of this headset is in emergency vehicles which use high level sirens to alert others of their approach. The modern electronic siren drives a compression type horn speaker with a square wave which rapidly varies in frequency. In the US the square wave varies from 700 to 1500 Hz and has several harmonics. The driver and passengers in the emergency vehicle are also exposed to this noise although the higher harmonics are greatly reduced in amplitude by the vehicle cab.

The noise creates several problems which include hearing damage, safety concerns and intelligible communications.

The risk of hearing damage to the occupants is real since the noise can easily exceed 85 dBA in the cab. The instant invention reduces that by 15 to 20 db for the user.

It is difficult for the driver to hear other sounds (especially other sirens) when the siren is active. This can lead to an increased risk of accidents. The instant invention allows for selective cancellation allowing other noises to be heard more easily with the headset on than with it off.

The siren sound lowers the intelligibility of all communications within the cab and through any communications system. With the instant invention the user is now in a quieter environment. Communications from others in the vehicle or from a radio speaker are easier to hear. If still better intelligibility is desired, the communications can be played through the same headset drivers (speakers) that are used to generate the anti-noise.

Insofar as the intelligibility of the outgoing communications/speech is concerned other solutions have been used. These include the close talking microphone which has been used traditionally. The microphone is built to be highly selective and acoustically cancels all sounds outside of its near field. The user either holds it close to his mouth while speaking or it is mounted in front of the mouth by a boom from the headset. The other solution to the problem has been the use of an "in-wire" technique. Here a third channel of noise cancellation is applied to the outgoing signal.

Figure 2:
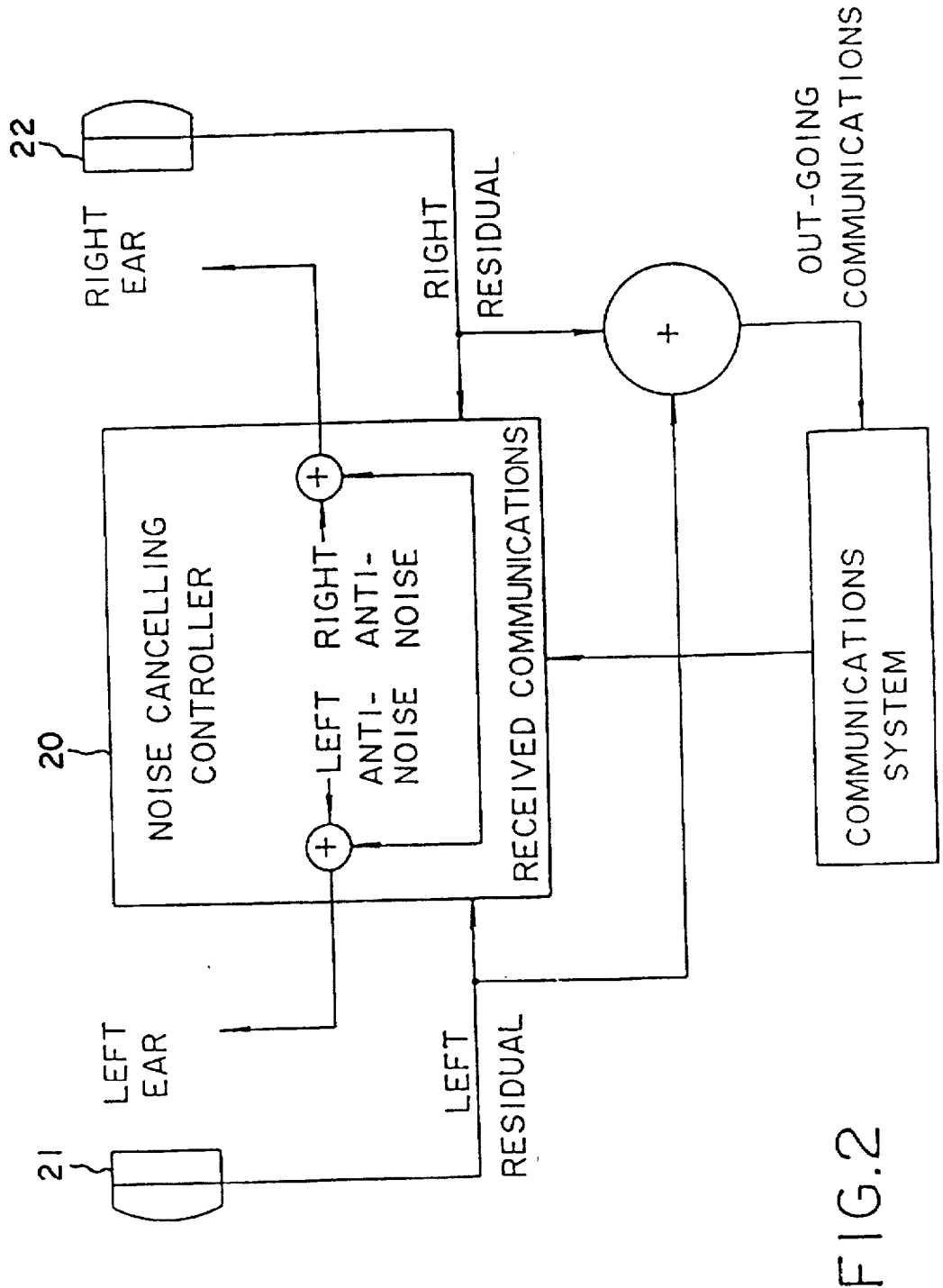
FIG. 2 shows a circuit for using residual microphones for communications

In the instant invention, the solution is cheaper, has no third channel, and is easier to use than a boom mounted microphone. FIG. 2 shows a diagrammatic flow chart of the system 20.

The system adds the two residual signals together at 20 and tends to improve the signal to noise in the out-going communications since the two speech signals tend to be in phase and the noise signals have random phase in the two residual signals.

The residual microphones 21, 22 are in a quiet environment due to the operation of the cancellation algorithm. They also respond to the wearer's speech since the open-back headset 17 does not attenuate speech. Therefore the residual signals can be used at the input for outgoing communications.

Thus the noise canceling headset and communications systems are fully integrated.

While only one embodiment of the instant invention has been shown it will be obvious to those of ordinary skill in the art that changes and modifications can be made without departing from the scope of the appended claims.

We claim:

1. A hands-free active noise canceling headset comprising:

clamping means adapted to secure the headset to the users head, at least one open back headset on said clamping means, said headset including a speaker means and a residual microphone means, and a controller means operatively connected to said speaker means and residual microphone means and adapted to both produce an anti-noise signal to said speaker means and adapted to receive signals from said residual microphone means representative of outward bound communications, wherein said controller means includes an LMS adapter, an adaptive filter means and an equalizer means to handle the anti-noise signals and communications signals from said residual microphone means.

2. A headset as in claim 1 in which said controller means is adapted to develop a reference signal by subtracting an equalized anti-noise signal of its own from the residual signal.

3. An active noise canceling headset for blocking out selected noises while permitting two way-communication, said headset comprising:

at least one open backed headset means adapted to produce a residual signal, control, means adapted to generate an anti-noise signal and operatively connected to said open backed headset means, and adaptive means within said control means adapted to produce a reference signal by subtracting an equalized version of its own anti-noise signal from the residual signal and produces an outward communication signal.

4. A headset as in claim 3 wherein said control means includes a Least Means Square adaptation means which has inherent compensation for any effects of feedback delays around the control means.

5. A headset as in claim 4 wherein said open backed headset means includes two residual microphones adapted to produce in phase signals and the control means adds the signals generated by said two microphones which improves the signal to noise ratio as the in phase signals are in place.

6. A headset as in claim 3 wherein said control means includes an equalizer means, an adaptive filler means and a Least Mean Square adapter means.

7. A headset as in claim 4 where the headset means and the control means are connected by a wire means.

* * * * *